United States Patent [19]

Moore

[11] Patent Number: 4,711,877

[45] Date of Patent: Dec. 8, 1987

[54] 6-PEN-VASOPRESSIN COMPOUNDS

[75] Inventor: Michael L. Moore, Media, Pa.

[73] Assignee: SmithKline Beckman Corporation, Philadelphia, Pa.

[21] Appl. No.: 777,385

[22] Filed: Sep. 18, 1985

[51] Int. Cl.[4] .................. A61K 37/34; C07K 7/16
[52] U.S. Cl. ............................ 514/11; 514/807; 530/315
[58] Field of Search .................. 530/315; 514/11, 807

[56] References Cited

U.S. PATENT DOCUMENTS

| 3,497,491 | 2/1970 | Zaoral et al. | 530/315 |
| 4,367,225 | 1/1983 | Manning et al. | 530/315 |
| 4,469,679 | 9/1984 | Huffman et al. | 530/315 |
| 4,469,680 | 9/1984 | Huffman et al. | 530/315 |
| 4,481,194 | 11/1984 | Ali et al. | 530/315 |
| 4,482,486 | 11/1984 | Brtnik et al. | 530/315 |
| 4,491,577 | 1/1985 | Manning et al. | 424/177 |
| 4,508,645 | 4/1985 | Simek et al. | 260/112.5 R |

FOREIGN PATENT DOCUMENTS 112809A 3/1983 European Pat. Off. .

OTHER PUBLICATIONS

Chem. Abstr., vol. 88 (1978), 676s.
F. L. Stassen et al., J. Pharmacology and Experimental Therapeutics, 223 53 (1982).

Primary Examiner—Delbert R. Phillips
Attorney, Agent, or Firm—Janice E. Williams; Stuart R. Suter; Alan D. Lourie

[57] ABSTRACT

Vasopressin derivatives having unexpected VSP site binding activity whose structures are characterized by a Mpr unit at position 1 and a Pen unit at position 6 are prepared by standard peptide synthetic methods also using an oxidative cyclization of a linear peptide dimercaptan. A representative species is [1-β-mercaptopropionic acid-2-(O-ethyl)-D-tyrosine-4-valine-6-penicillamine-8-arginine]vasopressin.

15 Claims, No Drawings

6-PEN-VASOPRESSIN COMPOUNDS

This invention relates to new cyclic peptides which have structures similar to that of vasopressin but distinguished by having a penicillamine (Pen) unit at the tertiary connecting position at 6 and a mercaptopropionic acid (Mpr) unit at position 1. The compounds have unexpected binding activity at vasopressin receptor sites.

BACKGROUND OF THE INVENTION

Synthetic modifications of the vasopressin or oxytocin structures are known to influence profoundly the antagonistic or agonistic activity of the resulting compounds. Predictability is poor in this area of research; F. L. Stassen et al., J. Pharmacology and Experimental Therapeutics, 223 53 (1982).

A. B. Ferring, European Patent No. 112,809A, discloses compounds with a Mpr unit at 1, a Cys at 6 and a VSP-antagonist tail which are described as oxytocin antagonists.

U.S. Pat. No. 4,508,645 describes structures which have a 6-Pen unit along with an amino containing unit at 1 such as Cys or Pen as well as an oxytocin-like tail. Such compounds have $V_1$-vasopressin antagonist activity.

U.S. Pat. No. 4,491,577 is representative of many prior art disclosures of vasopressin antagonists which have a 6-Cys unit structure.

I have now found that vasopressin-like compounds can be prepared whose structures have the bulky penicillamine unit at the tertiary 6-position. The resulting compounds have unexpected binding activity at vasopressin receptor sites.

In the description herein and in the claims, the nomenclature common in the art of peptide and, more specifically, vasopressin chemistry is used. When no confirguration is noted, the amino acid unit is in the L, or naturally occuring, form. The thio members of the β-mercaptopropionic acid (position 1) and penicillamine (position 6) units are added for clarity in certain structural formulas.

When the term, "vasopressin" or "VSP", is used, it means arginine vasopressin (AVP) unless otherwise modified.

"Alk" in formula I below and thereafter represents a lower alkyl of 1–4 carbons as a substituent which may be attached to the oxygen substituent of a tyrosine unit. Such alkyl substituents include methyl, ethyl, n-propyl, isopropyl or butyl. Preferably, Alk is methyl or ethyl.

Exemplary of the peptide art designations used herein are the following: Mpr, β-mercaptopropionic acid; OXT, oxytocin; Pro, proline; Pen, penicillamine; Gly, glycine; Tyr, tyrosine; Tyr(Alk), O-alkyltyrosine; Phe, phenylalanine; Phe(Alk), 4-alkylphenylalanine; Val, valine; Ile, isoleucine; Lys, lysine; Arg, arginine; Asn, asparagine; Tos, tosylate; BHA, benzhydrylamine; DIEA, diisopropylethylamine; 4-MeBzl, 4-methylbenzyl; TFA, trifluoroacetic acid; DCC, dicyclohexylcarbodiimide; HOBT, 1-hydroxybenzotriazole; ACM, acetamidomethyl.

DESCRIPTION OF THE INVENTION

The 6-Pen-vasopressin-like compounds of the invention are illustrated by the following structural formula:

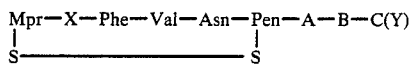

in which:
X is a D or L isomer of Ile, Phe(Alk), Tyr or Tyr(Alk);
A is Pro or a single bond;
B is a D or L-isomer of Arg or Lys;
C is a D or L isomer of Arg, Lys or Gly or a single bond; and
Y is OH or NH₂, or a pharmaceutically acceptable salt thereof.

A subgeneric group of the compounds of formula I are those in which X is D-Tyr(Et), B is Arg and Y is NH₂.

Also included in this invention are various derivatives of the compounds of formula I such as addition salts, prodrugs in ester form and complexes. The addition salts may be either salts with pharmaceutically acceptable cations such as $NH_4^\oplus$, $Ca^{\oplus\oplus}$, $K^\oplus$ or $Na^\oplus$ at a terminal acid group, when present, or with a pharmaceutically acceptable salt at a basic center of the peptide (as in the Arg or Lys units). The acetate salt forms are especially useful although hydrochloride, hydrobromide and salts with other strong acids are useful. In the isolation procedures outlined in the Examples, the peptide product is often isolated as the acetate salt. The compounds also form inner salts or zwitter ions as when a free terminal carboxy group is present.

Prodrugs are derivatives of the compounds of formula I which degrade to the parent compound in vivo. The ester prodrug forms are, for example, lower alkyl esters of the acids of formula I which have from 1–8 carbons in the alkyl radical or aralkyl esters which have 6–12 carbons in the aralkyl radical such as various benzyl esters. Ester derivatives of the compounds of formula I in which Y is OH are prepared by methods known in the art. Other latentiated derivatives of the compounds of formula I will be obvious to those skilled in the art. "Complexes" include various solvates, such as hydrates or alcoholates, or those with supporting resins, such as a Merrifield resin.

The compounds of formula I are prepared by cyclizing a linear peptide intermediate of this invention by means of the two mercapto groups located, respectively, in the penicillamine unit at position 6 and in the β-mercaptopropionic acid unit at position 1. The cyclization reaction occurs in the presence of a mild oxidizing agent which, at high dilution, is capable of oxidizing intramolecularly the dimercaptan to a disulfide.

Oxidation of the following linear peptide;

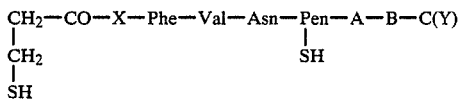

in which X, A, B, C and Y are as defined for formula I, is carried out as described generally above. For example, an excess of an alkali metal ferricyanide, such as potassium or sodium ferricyanide, is used. The linear intermediate is disssolved in a suitable unreactive solvent, preferably in an aqueous solvent, at a neutral pH, about 7–7.5. The reaction is run at ambient temperature, or lower, until substantialy complete. Lower alcohols, such as methanol, may be added. Preferably, the concentrations of the linear peptide dimercaptan and the oxidizing agent are low, say 0.01 molar concentration of oxidizing agent in several liters of aqueous solution to cyclize 1-6 grams of dimercaptan.

Other mild oxidation agents having an oxidation potential roughly equivalent to ferricyanide may also be used for the ring closure reaction. Oxygen, iodine, diiodoethane, hydrogen peroxide or cupric catalyzed oxygen are alternatives. Of course, one skilled in the art will recognize that certain cyclization methods are not appropriate if an interfering reaction site is present in the structure of the starting material of formula II. The linear mercaptan starting material may or may not have protecting groups common to the art present at the various amino acid units or at the mercapto positions. In the former case, the protecting groups are removed after cyclization. In the case of the ACM—SH protecting groups, removal of the protective group and cyclization may both be accomplished using iodine in aqueous methanol. Usually, however, the free linear peptide is cyclized.

The desired cyclic 6-Pen peptides of formula I are conveniently isolated by acidifying the aqueous oxidation mixture, such as using glacial acetic acid, and passing the reaction mixture over an ion-exchange chromatographic column, for example, over a weakly acid, acrylic resin column with acid elution, or by gel filtration over a bead-formed gel which has been prepared by cross-linking dextran with epichlorohydrin. Often, the acetate salt is isolated by these methods.

The linear peptide intermediates of formula II, in free or protected form, are conveniently prepared using solid-phase methods of peptide synthesis as discussed in M. Manning et al., J. Med. Chem. 25 46 (1982). A commercial benzhydrylamine support resin (BHR) is used to prepare the amide end products of formula I, i.e. in which C(Y) is Gly(NH$_2$) or NH$_2$ (the amides). A chloromethyl support resin (CMR) is used to prepare the acid compounds of formula I, i.e. in which C(Y) is Gly (OH) or OH (the acids). Solution or enzymatic synthetic methods can also be used.

The peptide chain of the linear peptides of formula II is built up, stepwise, proceeding from the C-terminal working toward the Mpr at position 1. Each unit is properly protected as known in the peptide art and as described below. The sequence of step reactions is conveniently carried out in a Beckman 990-B peptide synthesizer without isolation of each intermediate peptide. The details of the overall synthetic procedure are in the working examples presented hereinafter.

The various amino acids, which are consecutively added to the resin supported chain are protected as known to the art. For example, the Boc protecting group is used for an amino group especially at the α-position of the amino acid; ethylcarbamoyl, adamantyl, t-butyl, acetamidomethyl, trityl or an optionally substituted benzyl, for the mercapto groups at the propionic acid and Pen units; nitro; carbobenzoxy, methylene-2-sulfonyl or tosyl for the Arg unit; and ethyloxycarbonyl or an optionally substituted carbobenzoxy(Z) for the Tyr or Lys units. The protective groups should, most conveniently, be those which are easily removed, such as using acid treatment for tert.butyloxycarbonyl (Boc), sodium-liquid ammonia or modified catalytic hydrogenation for benzyl or carbobenzoxy groups.

The protected linear peptide intermediate is split from the carrying resin matrix, for example, by using ammonia in an aqueous miscible solvent, and then, is treated to remove the protective groups, such as by using sodium-liquid ammonia. This procedure gives the amide derivative of the linear peptide dimercaptan (II).

More conveniently, the two steps are combined by treating the resin supported peptide with anhydrous hydrogen fluoride using a suitable carbonium ion scavenger, such as anisole, to give the Mpr$^1$-Pen$^6$ peptide intermediate of formula II in good yield.

The compounds of this invention have V$_1$-V$_2$ vasopressin antagonist activity. Vasopressin is primarily known to contribute to the anti-diuretic mechanism of action within the kidney. When the action of these compounds antagonizes that of the natural anti-diuretic hormone (ADH), the body excretes water due to an increased permeability of the terminal portions of the renal tubule. This mechanism of action is at the vasopressin receptors (V$_2$-receptors) located on the plasma membrane of certain renal epithelial cells.

Any patient suffering from the syndrome of inappropriate antidiuretic hormone secretion (SIADH) or from an undesirable edematous condition is a target for compounds which have substantial V$_2$-antagonist activity. Examples of clinical conditions indicated for such compounds include hypertension, hepatic cirrhosis, congestive heart failure or a component of any traumatic condition resulting from serious injury or disease.

The second group of vasopressin receptors, which are secondary targets of this invention, are those affecting the smooth muscle tissues of the blood vessels. Vasopressin is natural stimulant of these effectors which results in pressor effects on the cardiovascular system. These receptors are called generically V$_1$ receptors for the purposes of this disclosure.

The compounds of this invention, therefore, are mainly used for binding at the vasopressin receptor sites in patients in need of such treatment by administration internally, particularly parenterally or by insufflation, to said patients. A nontoxic but effective quantity of the chosen compound is preferably combined with a pharmaceutical carrier. Dosage units contain a nontoxic, effective quantity of the active ingredient which is selected from the range 0.25–50 mcg/kg, preferably 3–15 mcg/kg, based on a 70 kg patient. The dosage units are administered from 1 to 5 times daily or by continuous intravenous drip.

The pharmaceutical compositions of this invention, which contain an active ingredient of formula I, comprise a dosage unit quantity as described above dissolved or suspended in a standard liquid carrier. Such a carrier is isotonic saline. The composition is often used in an ampoule or a multiple dose vial suitable for parenteral injection, such as for intravenous, subcutaneous or intramuscular administration. A composition for insufflation may be similar but is often administered in a metered dose applicator or inhaler. Pulverized powder compositions may be used along with oily preparations, gels, buffers for isotonic preparation, emulsions or aerosols.

The binding activity in hog and rat liver tissue, as well as the antagonistic activity in the hydropenic rat, of the compounds according to this invention is illustrated by the following results which were obtained using testing protocols which are described in the literature [F. Stassen, J. Pharmacology and Experimental Therapeutics, 223 50 (1982)]:

Compound A,
Mpr—D-Tyr(Et)—Phe—Val—Asn—Pen—Pro—Arg—Gly(NH$_2$)
Compound B,
Mpr—D-Tyr(Et)—Phe—Val—Asn—Cys—Pro—Arg—Gly(NH$_2$)

|  | $K_B$ (hog) | $K_B$ (rat liver) | ED$_{300}$ (hydropenic rat) |
|---|---|---|---|
| Compound A | 190 nM | 110 nM | 16.6 μg/kg; 130.4 μg/kg |
| Compound B | 9900 nM | — | — |

These data indicate that a representative compound of this invention (A) is about 50 times more active than is a compound (B) which is identical at all units save at the critical 6-position. Compound B has a cysteine unit at this position as do most vasopressin agonist or antagonist congeners of the art. The structure of compound A of the present invention is distinguished by a bridgehead penicillamine unit and a position 1 β-mercaptopropionic acid.

The following examples are intended solely to teach the preparation and use of the compounds of this invention. All temperatures are in degrees Centigrade.

EXAMPLE 1

Boc-L-(S-p-methylbenzyl)penicillamine 5.0 G of L-penicillamine (33.6 mmol) was dissolved in 5 ml of water containing 1.3 g of sodium hydroxide (33.6 mmol, 1 eq.). To this was added 10 ml of tert.-butanol. 8.0 G of di-tert.-butylcarbonate (37 mmol, 1.1 eq.) was added dropwise over 30 minutes. The reaction was allowed to proceed at room temperature for 6 hours. The turbid reaction mixture was diluted with 50 ml of water and extracted with hexane (3×50 ml), acidified to pH 3 with solid sodium bisulfate and extracted with ethyl acetate (3×50 ml). The combined ethyl acetate extracts were dried over sodium sulfate and, then, evaporated to dryness, yielding 8.0 g of Boc-L-penicillamine (96%): nmr (CDCl$_3$) 1.45 ppm and 1.57 ppm, over-lapping singlets, t-butyl and beta-dimethyl protons, 4.32 ppm, br. doublet, alpha proton.

8.0 G of Boc-L-penicillamine (32 mmol) was dissolved in 100 ml of liquid ammonia cooled in an icesalt bath. To this was added small pieces of lithium wire until a blue color persisted. 5.95 G of p-methylbenzyl bromide (32 mmol, 1 eq.) dissolved in 5 ml of ethyl ether was added dropwise to the ammonia mixture over 15 minutes. The reaction mixture was allowed to warm to room temperature. The ammonia was blown off with a stream of dry nitrogen. The residue was dissolved in water, extracted with hexane (3×50), acidified to pH 3 with solid sodium bisulfate and extracted with ethyl acetate (3×50 ml). The combined ethyl acetate extracts were dried over sodium sulfate and evaporated to dryness, yielding 10.1 g (89%) of the titled product as an oil: nmr (CDCl$_3$) 1.59 ppm, singlet, 15H, t-butyl +beta dimethyl; 2.13 ppm, singlet, 3H, methyl group; 3.59, s, 2H, methylene; 7.00 ppm, dd, 4H, aromatic ring.

EXAMPLE 2

Solid Phase Synthesis of Linear Peptide-BHA Resin Starting Material

For the solid phase synthesis of the titled resin-supported peptides, a terminal position unit-resin material, for example, Boc-Gly BHA resin (1.00 mmol/g of resin), was used as a starting material. It was prepared by reacting Boc-Amino Acid-(Tos if necessary), (3 mmol), with the benzhydrylamine resin, (1.0 mmol), in methylene chloride or dimethylformamide for two hours. The benzhydrylamine resin as a free base was swelled in methylene chloride overnight. It was washed once with 7% diisopropylethylamine (DIEA) in methylene chloride, then 6×1 min. with methylene chloride, and finally 2×1 min. with predried dimethylformamide. The loading of BOC-amino acid on the resin was carried out twice on the shaker using 1-hydroxybenzotriazole (HOBT, 3 mmol), and dicyclohexylcarbodiimide (DCC, 3 mmol). A quantitative ninhydrin test and amino acid analysis were performed routinely after loading to determine the percentage loading on the resin.

The appropriately protected amino acids were coupled sequentially on the Boc-amino acid-resin using the Beckman peptide synthesizer 990-B or a shaker. The program used for each coupling, except Boc-Asn and Mpr(4-MeBzl), was as follows:

(1) Washed with methylene chloride (3 times, 1 min).
(2) Prewashed with 50% trifluoroacetic acid in methylene chloride (1 time, 1 min).
(3) Deprotection with 50% trifluoroacetic acid in methylene chloride (20 min).
(4) Washed with methylene chloride (3 times, 1 min).
(5) Prewashed with 7% DIEA in methylene chloride (1 time, 1 min).
(6) Neutralized with 7% DIEA in methylene chloride (1 time, 10 min).
(7) Washed with methylene chloride (3 times, 1 min).
(8) Protected amino acid (3 mmol) in methylene chloride, followed by addition of DCC, 3 mmol, 10 ml of 0.3 M in methylene chloride, and coupling for two hours.
(9) Washing with methylene chloride (3 times, 1 min).
(10) Washing with ethanol/methylene chloride (1:1) (3 times, 1 min).
(11) Washing with methylene chloride (3 times, 1 min).

In case of coupling of Asn moiety, 1-hydroxybenzotriazole (HOBT, 3 mmol) was used, 10 ml of 0.3 M in dimethylformamide. Dry dimethylformamide was also used as solvent when Mpr(4-MeBzl) was coupled onto the peptide resin, using 4-dimethylaminopyridine (DAP, 3 mmol). Completion of each coupling reaction was monitored by the ninhydrin test. The p-methylbenzyl group was used to protect the thiol groups of penicillamine and β-mercaptopropionic acid.

The benzhydrylamine resin was analyzed by nitrogen analysis to fall within 0.72–1.03 mmol per 1 gram. Each protected amino acid unit was purchased from commercial sources or synthesized by known procedures. Successful coupling incorporated 0.4 to 0.732 mmole per gram of the first amino acid.

EXAMPLE 3

Mpr—D—Tyr(Et)—Phe—Val—Asn—Pen—Pro—Arg—Gly(NH$_2$)

The resin supported peptide was synthesized as described generally in Example 2, by the standard solid phase method using benzhydrylamine resin as the support. The t-butyloxycarbonyl group was used for temporary amine protection. The guanidine of arginine was protected as the tosyl derivative and the sulfhydryls were protected as the p-methylbenzyl thioethers. Couplings were usually performed in CH$_2$Cl$_2$/DMF using DCC/HOBT. Deprotection was with 50% TFA/CH₂Cl₂.

The peptidyl resin (1 mmol) from Example 2 was treated with 15 ml of hydrogen fluoride and 1 ml of anisole at 0° for one hour. After removal of the HF, the resin was washed with ethyl ether. The filter funnel containing the resin was mounted on a 4l filter flask containing 3l of water and was then extracted with 50% HOAc (2×50 ml), 50% DMF (aq) (2×50 ml) and water (50 ml) in such a way that the extracts were immediately diluted. The pH of the solution was adjusted to 7.2 with 50% of alkali solution. A solution of 0.01 M potassium ferricyanide was added dropwise with stirring until a yellow color persisted (130 ml, 130% of theory). The pH was adjusted to 4.5 with glacial acetic acid. The solution was filtered through a filter aid and pumped over an acrylic ester resin column of intermediate polarity (XAD-7). The column was washed with water and eluted with 200 ml of 50% acetonitrile/water with 1% trifluoroacetic acid. The eluant was evaporated to dryness and was lyophilized from 1% HOAc to give 754 mg of crude titled peptide.

A 100 mg aliquot of the crude peptide was purified by partition chromatography (n-BuOH/HOAc/H₂, 4:1:5) followed by filtration on a dextran-epichlorohydrin gel (Cephadex G-15) (1% HOAc), yielding 12.8 mg purified peptide: homogeneous by tlc and hplc, FAB MS m/z 1096 (M+H⁺); amino acid analysis-aspartic acid 1.00, proline 0.57, glycine 1.12, tyrosine 0.88, phenylalanine 0.95, arginine 1.09, valine +penicillamine 1.77; peptide content 73.4%

EXAMPLE 4

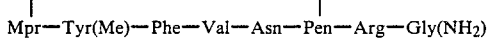

Mpr—Tyr(Me)—Phe—Val—Asn—Pen—Arg—Gly(NH₂)

The protected peptide intermediate resin, Mpr-(4-MeBz)-Tyr(Me)-Phe-Val-Asn-Pen(4-MeBz)-Arg(Tos)-BHA resin [1.85 g, obtained from 1.0 mmol/g amine/resin (N₂-analysis) using a Beckman peptide synthesizer], is reacted with anhydrous hydrogen fluoride (30 ml) in the presence of 3.0 ml of anisole at 0° for 50 minutes. After evaporation in vacuo to dryness, the residue is treated with anhydrous diethyl ether. The crude peptide is extracted with dimethylformamide (90 ml) and 33% acetic acid (90 ml) into 3.5l of de-aerated water previously adjusted to pH 4.5. The aqueous diluted disulfhydryl octapeptide is cyclized using 0.01 M potassium ferricyanide solution at pH 7.12 until color persists for 30 minutes. After the completion of the oxidation reaction, the pH of the solution is adjusted to 4.5 using glacial acetic acid. This solution is passed through a weakly acid, acrylic resin (Bio-Rex 70) column (2.5×12 cm) slowly. The column is eluted with pyridine-acetate buffer (30:4:66, pyridine/glacial acetic acid/water). The pyridine acetate solution is then removed by distillation in vacuo. The residue was lyophilized from 5% acetic acid to give the titled peptide which is purified as described above.

EXAMPLE 5

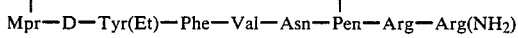

Mpr—D—Tyr(Et)—Phe—Val—Asn—Pen—Arg—Arg(NH₂)

The protected peptide-resin, Mpr(4-MeBzl)-D-Tyr-(Et)-Phe-Val-Asn-Pen(4-MeBzl)-Arg(Tos)-Arg(Tos)-BHA-resin (2.0 g, obtained from 1.0 mmol/g of amine/resin), is reacted with 30 ml of anhydrous hydrogen fluoride in the presence of 3.0 ml of anisole at 0° for 50 minutes. After evaporation in vacuo to dryness, the residue is treated . with anhydrous diethyl ether. The crude peptide is extracted with dimethylformamide (75 ml), and 33% acetic acid (75 ml) and taken into 3.5 liter of de-aerated water which had been previously adjusted to pH 4.5. The aqueous diluted disulfhydryl linear peptide is oxidatively cyclized using 0.01 M potassium ferricyanide solution at pH 7.12 until color persists for 30 minutes. After the completion of the oxidation reaction, the pH of the solution is adjusted to 4.5 using glacial acetic acid. This solution is passed through a weakly acid acrylic resin (Bio-Rex-70) column (2.5×10 cm) slowly. The column is eluted with pyridine-acetate buffer (30:4:66), pyridine/HOAc/H₂O) The pyridine acetate solution is removed in vacuo. The residue is lyophilized from 10% acetic acid to give the crude titled peptide which is purified as above.

EXAMPLE 6

Procedure For The General Synthesis Of The Acid End

Products (I, Y is OH)

Boc-AA-Merrifield resin is made by coupling a Boc-AA to Merrifield resin using the known cesium salt method to give Boc-AA-OCH₂C₆H₄-resin which is used as the starting material for the synthesis. The synthesis is carried out on the Beckman 990-B peptide synthesizer using the following protocol. Three equivalents of each of the amino acids are dissolved in their appropriate solvents [for example, the Boc derivatives of S-4-MeBzl-Pen, Val, Phe and S-4-MeBzl-Mpr in methylene chloride, Asn in dimethylformamide, D-Tyr(Et) or BrZ-D-Tyr in 1:1 methylene chloride/dimethylformamide]and are coupled using an equimolar amount of dicyclohexylcarbodiimide (DCC) and 1-hydroxybenzotriazole (HOBT) except for the coupling of S-4-MeBzl-Mpr where 1.0 equivalent of dimethylaminopyridine is used as catalyst. The extent of coupling is determined by qualitative ninhydrin analyses of each aliquot sample and couplings are repeated when necessary. The Boc groups are removed using 1:1 trifluoroacetic acid/methylene chloride and, after washing, the free amine is generated using 5% diisopropylethylamine/methylene chloride. The sequence of the peptide is checked using solid phase sequencing before coupling of the S-4-MeBzl-Mpr and its homogeneity confirmed. After the final coupling, the peptide is dried to give the peptide-resin.

1.1 G (0.5 mmole) of the peptide resin with 3 ml of anisole is stirred 60 minutes at 0° (ice bath) in 25 ml of anhydrous liquid hydrogen fluoride (HF). The HF is, then, removed under reduced pressure at 0°. The residue is washed with ethyl ether and the peptide eluted with dimethylformamide, 20% acetic acid and 0.3 N ammonium hydroxide.

The filtrate is added to 2l of degassed water and the pH adjusted to 7.1 with conc. ammonium hydroxide. A 0.01 M solution of potassium ferricyanide is then added dropwise with stirring until a faint yellow color persisted (about 41 ml).

The resulted solution is then passed through a flash column (5 cm×15 cm) of a packing of silica gel coated with a C-18 silane. The column is, then, washed with 350 ml of water and the petide eluted with 500 ml of 1:1 acetonitrile/water (0.25% trifluoroacetic acid) in 20 ml fractions.

Product containing fractions (TLC) are combined and concentrated. The residue is dissolved in conc. acetic acid, diluted with water and lyophilized to yield the acid peptide.

Using this method, the following peptides are prepared:

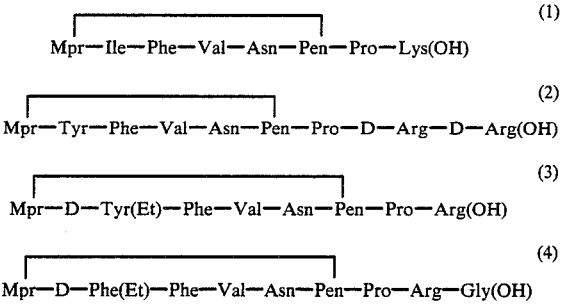

EXAMPLE 7

Parenteral Dosage Unit Compositions

A preparation which contains 50 mcg of the cyclic peptide of Example 3 as a sterile dry powder for parenteral injection is prepared as follows: 10 mcg of the peptide amide is dissolved in 1 ml of an aqueous solution of 20 mg of mannitol. The solution is filtered under sterile conditions into a 2 ml ampoule and lyophylized. The powder is reconstituted before either intramuscular or intravenous injection to a subject suffering from hypertension or shock susceptible to anti-ADH mechanism of action. The injection is repeated as necessary, from 1–5 times daily or in continuous i.v. drug injection. Other G-Pen peptides of this invention are made up and used in like manner.

Nasal Dosage Unit Compositions

30 Milligrams of finely ground 6-Pen peptide of this invention such as the product of Example 3 is suspended in a mixture of 75 mg of benzyl alcohol and 1.395 g of a suspending agent such as a commercial mixture of semi-synthetic glycerides of higher fatty acids. The suspension is placed in an aerosol 10 ml container which is closed with a metering valve and charged with aerosol propellants. The contents comprise 100 unit doses which are administered intranasally to an edematous subject from 1–6 times a day.

What is claimed is:

1. A polypeptide compound having the formula:

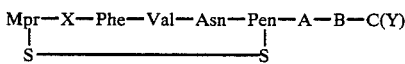

in which:
  X is a D or L isomer of Ile, Phe(Alk), Tyr or Tyr-(Alk);
  A is Pro or a single bond;
  B is a D or L isomer of Arg or Lys;
  C is a D or L isomer of Arg, Lys or Gly or a single bond; and
  Y is OH or NH$_2$, or a pharmaceutically acceptable salt or ester prodrug thereof.

2. A compound of claim 1 in which Y is NH$_2$.
3. A compound of claim 1 in which X is D-Tyr-(Et).
4. A compound of claim 1 in which X is the D isomer of Tyr or Tyr(Alk).
5. A compound of claim 1 in which B and C are Arg and Y is NH$_2$.
6. A compound of claim 1 having the structural formula:

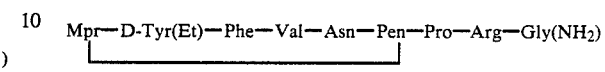

7. A compound of claim 1 having the structural formula:

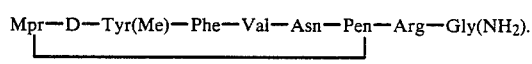

8. A compound of claim 1 having the structural formula:

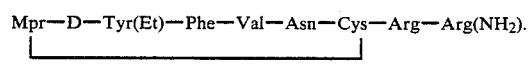

9. A pharmaceutical composition having vasopressin antagonist activity comprising a pharamceutical carrier and, dispersed therein, an effective therefor but nontoxic quanitity of a compound of claim 1.
10. A composition of claim 9 in which the compound is:

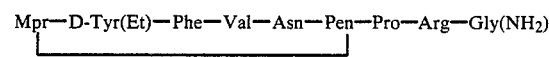

11. A composition of claim 9 in which the compound is:

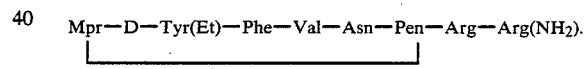

12. A composition of claim 12 in which the compound is:

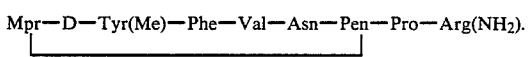

13. The method of producing vasopressin antagonist activity in a patient in need thereof which comprises administering partenterally of intranasally to said patient a nontoxic, effective therefor quantity of a compound of claim 1.
14. The method of claim 13 in which the compound is:

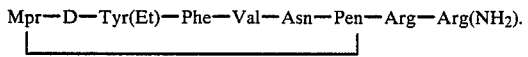

15. The method of claim 13 in which the compound is:

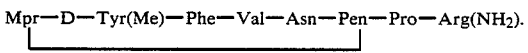

* * * * *